US011302447B1

(12) United States Patent
Malone

(10) Patent No.: US 11,302,447 B1
(45) Date of Patent: *Apr. 12, 2022

(54) SYSTEMS AND METHODS FOR SIMULATING MECHANISMS OF INJURY UTILIZING AN OBJECTIVE IMPAIRMENT INJURY SCORE RISK MODEL

(71) Applicant: MedPros, LLC, Warner Robins, GA (US)

(72) Inventor: K. Scott Malone, Warner Robins, GA (US)

(73) Assignee: MedPros, LLC, Warner Robins, GA (US)

( * ) Notice: Subject to any disclaimer, the term of this patent is extended or adjusted under 35 U.S.C. 154(b) by 305 days.

This patent is subject to a terminal disclaimer.

(21) Appl. No.: 16/695,034

(22) Filed: Nov. 25, 2019

Related U.S. Application Data

(63) Continuation-in-part of application No. 16/448,769, filed on Jun. 21, 2019, now Pat. No. 11,132,750.

(51) Int. Cl.
| | |
|---|---|
| G16H 50/30 | (2018.01) |
| G16H 10/20 | (2018.01) |
| G16H 10/60 | (2018.01) |
| G16H 50/50 | (2018.01) |
| G16H 15/00 | (2018.01) |
| G06N 20/00 | (2019.01) |
| G06T 13/80 | (2011.01) |

(52) U.S. Cl.
CPC ............ *G16H 50/30* (2018.01); *G06N 20/00* (2019.01); *G06T 13/80* (2013.01); *G16H 10/20* (2018.01); *G16H 10/60* (2018.01); *G16H 15/00* (2018.01); *G16H 50/50* (2018.01); *G06T 2200/24* (2013.01)

(58) Field of Classification Search
CPC ............................... G06Q 40/00; G16H 10/00
USPC .......................................................... 705/35
See application file for complete search history.

(56) References Cited

U.S. PATENT DOCUMENTS

| | | | | |
|---|---|---|---|---|
| 5,687,968 | A | * | 11/1997 | Tarantino ............... A63F 3/081 273/139 |
| 6,098,051 | A | * | 8/2000 | Lupien ................. G06Q 40/12 705/36 R |
| 6,272,474 | B1 | * | 8/2001 | Garcia ................. G06Q 40/00 705/35 |

(Continued)

*Primary Examiner* — Kirsten S Apple
(74) *Attorney, Agent, or Firm* — FisherBroyles, LLP

(57) ABSTRACT

Various embodiments are directed to simulating mechanisms of injury utilizing an objective impairment injury score risk model. A computing device may receive injury data from a user. The computing device may perform a security action that protects against unauthorized sharing of the injury data by storing the injury data as a group of linked blocks in a distributed computing system. The computing device may utilize a machine-learning model to generate a set of questions for the user. The questions may be utilized to determine weighting factors associated with the injury data. The computing device may utilize the machine-learning model to determine an impairment injury score based on the weighting factors. The computing device may display an injury risk management report to the user. The computing device may display, based at least in part on the report, a simulation describing a mechanism of the injury described in the injury data.

20 Claims, 9 Drawing Sheets

(56) References Cited

U.S. PATENT DOCUMENTS

| | | | | |
|---|---|---|---|---|
| 6,278,982 B1* | 8/2001 | Korhammer | G06Q 40/04 | 705/36 R |
| 6,356,911 B1* | 3/2002 | Shibuya | G01C 21/3446 | |
| 6,721,715 B2* | 4/2004 | Nemzow | G06Q 40/00 | 705/35 |
| 7,062,361 B1* | 6/2006 | Lane | F25D 29/00 | 700/291 |
| 7,130,789 B2* | 10/2006 | Glodjo | G06Q 20/10 | 705/37 |
| 7,315,840 B1* | 1/2008 | Keith | G06Q 40/00 | 705/35 |
| 7,392,213 B2* | 6/2008 | Merkoulovitch | G06Q 40/06 | 705/36 R |
| 7,831,494 B2* | 11/2010 | Sloan | G06Q 40/025 | 705/36 R |
| 8,073,763 B1* | 12/2011 | Merrin | G06Q 40/04 | 705/37 |
| 8,126,794 B2* | 2/2012 | Lange | G06Q 30/08 | 705/36 R |
| 8,359,260 B2* | 1/2013 | Merrin | G06Q 40/00 | 705/37 |
| 8,417,618 B2* | 4/2013 | Milne | G06Q 40/04 | 705/37 |
| 8,755,943 B2* | 6/2014 | Wenzel | G05D 23/1917 | 700/276 |
| 2002/0147671 A1* | 10/2002 | Sloan | G06Q 40/025 | 705/36 R |
| 2002/0147675 A1* | 10/2002 | Das | G06Q 40/04 | 705/37 |
| 2002/0194099 A1* | 12/2002 | Weiss | G06Q 40/08 | 705/36 R |
| 2003/0182224 A1* | 9/2003 | Horrigan | G06Q 40/04 | 705/37 |
| 2004/0024692 A1* | 2/2004 | Turbeville | G06Q 40/08 | 705/38 |
| 2005/0080703 A1* | 4/2005 | Chiesa | G06Q 40/04 | 705/36 R |
| 2005/0124408 A1* | 6/2005 | Vlazny | G07F 17/3288 | 463/28 |
| 2008/0015871 A1* | 1/2008 | Eder | G06Q 10/067 | 706/21 |
| 2009/0106140 A1* | 4/2009 | De La Motte | G06Q 40/06 | 705/37 |
| 2009/0307149 A1* | 12/2009 | Markov | G06Q 40/00 | 705/36 R |
| 2010/0088210 A1* | 4/2010 | Gardner | G06Q 40/00 | 705/35 |
| 2011/0119166 A1* | 5/2011 | Steinberg | G06Q 10/06 | 705/34 |
| 2012/0239453 A1* | 9/2012 | Osogami | G06Q 50/06 | 705/7.25 |
| 2012/0323753 A1* | 12/2012 | Norman | G06Q 40/00 | 705/37 |
| 2013/0275334 A1* | 10/2013 | Andersen | G06Q 40/06 | 705/36 R |
| 2014/0201110 A1* | 7/2014 | Sato | G06Q 50/06 | 705/412 |
| 2015/0058261 A1* | 2/2015 | Parikh | G06F 1/3209 | 705/412 |
| 2015/0310461 A1* | 10/2015 | Lee | G06Q 10/04 | 705/412 |
| 2015/0363866 A1* | 12/2015 | Depew | G06Q 30/0633 | 705/26.8 |
| 2016/0117784 A1* | 4/2016 | Hwang | G06Q 30/0283 | 705/412 |
| 2016/0196521 A1* | 7/2016 | Wada | G06Q 50/06 | 705/7.25 |
| 2018/0074523 A1* | 3/2018 | Cantrell | G05D 1/104 | |

* cited by examiner

SYSTEMS AND METHODS FOR SIMULATING MECHANISMS OF INJURY UTILIZING AN OBJECTIVE IMPAIRMENT INJURY SCORE RISK MODEL

CROSS REFERENCE TO RELATED APPLICATION

This application is a continuation-in-part of U.S. application Ser. No. 16/448,769, filed Jun. 21, 2019, the disclosure of which is incorporated, in its entirety, by this reference.

BACKGROUND

Risk managers (e.g., in the healthcare industry, insurance industry and employers) are often required to obtain a determination of the degree of impairment and associated disability from injuries incurred during an individual's employment and/or in the performance of their professional duties. The injuries may be on a scale of a non-reportable minor medical injury to a complete catastrophic injury leaving an individual unemployable for suitable and sustainable occupational work thus totally disabled.

The concept of determining a medical and physical impairment is as much an art as a science. Physicians are often required to review medical records, ask injured parties (e.g., athletes) about current problems, examine their bodies, and review diagnostic studies. Predicting who will stay healthy and who will get hurt is an art. It is even more difficult to determine permanent functional impairments as a result of injuries. Conventional systems for assessing injuries in athletes are based on systems such as the American Medical Association (AMA) guidelines. However, the AMA guides only provide a framework for impairments. The AMA guides assumes every profession is the same (i.e., apples to apples). Thus, AMA impairment ratings do not adequately take into account the impact of an individual's impairment on his or her job performance. In particular, the impairment incurred as a result of injury may lead to a detrimental effect on an individual's career. For example, a professional athlete or entertainer incurring an injury during a game or a performance may file an insurance claim to recover compensation in the form of current and future expenses (e.g., medical bills and costs), losses in the form of lost income or lost wages, pain and suffering damages, and/or emotional distress damages, based on an assessment of impairment and or disability associated with the injury. Furthermore, traditional methods for assessing impairment often include the use of subjective approaches (e.g., computations and algorithms) configured to assist in the calculation of insurance claim settlements. As mentioned above, one of the primary problems with these approaches is that they are not designed to take into account various injury related variables such as the occupation of an injured party, employment duties, and/or the loss of supplemental income. It is with respect to these considerations and others that the various embodiments of the present invention have been made.

SUMMARY

As will be described in greater detail below, the instant disclosure describes various systems and methods for utilizing an objective injury impairment score risk model.

In one example, a method for simulating mechanisms of injury utilizing an objective impairment injury score risk model may include (1) receiving, by a computing device, injury data from a user, (2) performing, by the computing device, a security action that protects against unauthorized sharing of the injury data by storing the injury data as a plurality of linked blocks in a distributed computing system, (3) generating, by the computing device and utilizing a machine-learning model, one or more questions for the user, where the questions are utilized for receiving user answers to determine a plurality of weighting factors associated with the injury data, (4) determining, by the computing device and utilizing the machine-learning model, an impairment injury score based on the injury data and the weighting factors, where the impairment injury score includes an objectively determined value associated with a degree of impairment resulting from an injury described in the injury data, (5) displaying, by the computing device, an injury risk management report based on the impairment injury score to the user, and (6) displaying, by the computing device and based at least in part on the injury risk management report, a simulation describing a mechanism of the injury described in the injury data.

In some examples, displaying the simulation describing the mechanism of the injury may include (1) retrieving one or more relational factors associated with the injury from the injury data, and (2) displaying the simulation based on the relational factors. In some embodiments, the relational factors may include at least one of (1) patient related factors associated with an injured party, (1) psychosocial factors associated with the injured party, (3) extrinsic factors associated with the injured party, or (4) economy factors associated with the injured party. In some examples, the relational factors may be utilized to determine a potential for incurring the injury described in the injury data.

In some embodiments, displaying the simulation describing the mechanism of the injury may include generating an animation of a traumatic event causing at least one of (1) a spinal injury, (2) a musculoskeletal injury, or (3) an internal organ injury. In some examples, generating the animation of the traumatic event may include animating at least one of (1) a blunt force trauma applied to at least one body part, (2) a shearing force trauma applied to the at least one body part, or (3) a compression force trauma applied to the at least one body part. In some embodiments, the blunt force trauma may include a secondary penetration injury to the at least one body part.

In some examples, generating the animation of the traumatic event may include animating at least one of (1) a hyperextension of at least one body part, (2) a hyperflexion of the at least one body part, (3) a rotational force applied to the at least one body part, (4) a lateral force applied to the at least one body part, or (5) a distraction force caused by an excessive stretching of the at least one body part. In some embodiments, generating the animation of the traumatic event may include animating at least one of (1) a twisting injury, (2) a squatting injury, or (3) an injury caused by a change in position. In some embodiments, generating the animation of the traumatic event may include animating a non-contact injury.

In one example, a system for simulating mechanisms of injury utilizing an objective impairment injury score risk model may include at least one processor and a memory storing computer-executable instructions that when executed by the at least one processor, cause the system to (1) receive, by a computing device, injury data from a user, (2) perform, by the computing device, a security action that protects against unauthorized sharing of the injury data by storing the injury data as a plurality of linked blocks in a distributed computing system, (3) generate, by the computing device and utilizing a machine-learning model, one or more questions for the user, where the questions are utilized for receiving user answers to determine a group of weighting factors associated with the injury data, (4) determine, by the computing device and utilizing the machine-learning model, an impairment injury score based on the injury data and the weighting factors, where the impairment injury score includes an objectively determined value associated with a degree of impairment resulting from an injury described in the injury data, (5) display, by the computing device, an injury risk management report based on the impairment injury score to the user, and (6) display, by the computing device and based at least in part on the injury risk management report, a simulation describing a mechanism of the injury described in the injury data.

In some examples, displaying the simulation describing the mechanism of the injury may include (1) retrieving one or more relational factors associated with the injury from the injury data, and (2) displaying the simulation based on the relational factors. In some embodiments, the relational factors may include at least one of (1) patient related factors associated with an injured party, (1) psychosocial factors associated with the injured party, (3) extrinsic factors associated with the injured party, or (4) economy factors associated with the injured party. In some examples, the relational factors may be utilized to determine a potential for incurring the injury described in the injury data.

In some embodiments, displaying the simulation describing the mechanism of the injury may include generating an animation of a traumatic event causing at least one of (1) a spinal injury, (2) a musculoskeletal injury, or (3) an internal organ injury. In some examples, generating the animation of the traumatic event may include animating at least one of (1) a blunt force trauma applied to at least one body part, (2) a shearing force trauma applied to the at least one body part, or (3) a compression force trauma applied to the at least one body part. In some embodiments, the blunt force trauma may include a secondary penetration injury to the at least one body part.

In some examples, generating the animation of the traumatic event may include animating at least one of (1) a hyperextension of at least one body part, (2) a hyperflexion of the at least one body part, (3) a rotational force applied to the at least one body part, (4) a lateral force applied to the at least one body part, or (5) a distraction force caused by an excessive stretching of the at least one body part. In some embodiments, generating the animation of the traumatic event may include animating at least one of (1) a twisting injury, (2) a squatting injury, or (3) an injury caused by a change in position. In some embodiments, generating the animation of the traumatic event may include animating a non-contact injury.

In some examples, the above-described method may be encoded as computer-readable instructions on a non-transitory computer-readable medium. For example, a non-computer-readable medium may include one or more computer-executable instructions that, when executed by at least one processor of a computing device, may cause the computing device to (1) receive, by the computing device, injury data from a user, (2) perform, by the computing device, a security action that protects against unauthorized sharing of the injury data by storing the injury data as a plurality of linked blocks in a distributed computing system, (3) generate, by the computing device and utilizing a machine-learning model, one or more questions for the user, where the questions are utilized for receiving user answers to determine a group of weighting factors associated with the injury data, (4) determine, by the computing device and utilizing the machine-learning model, an impairment injury score based on the injury data and the weighting factors, where the impairment injury score includes an objectively determined value associated with a degree of impairment resulting from an injury described in the injury data, (5) display, by the computing device, an injury risk management report based on the impairment injury score to the user, and (6) display, by the computing device and based at least in part on the injury risk management report, a simulation describing a mechanism of the injury described in the injury data.

In some examples, displaying the simulation describing the mechanism of the injury may include (1) retrieving one or more relational factors associated with the injury from the injury data, and (2) displaying the simulation based on the relational factors. In some embodiments, the relational factors may include at least one of (1) patient related factors associated with an injured party, (1) psychosocial factors associated with the injured party, (3) extrinsic factors associated with the injured party, or (4) economy factors associated with the injured party. In some examples, the relational factors may be utilized to determine a potential for incurring the injury described in the injury data.

In some embodiments, displaying the simulation describing the mechanism of the injury may include generating an animation of a traumatic event causing at least one of (1) a spinal injury, (2) a musculoskeletal injury, or (3) an internal organ injury. In some examples, generating the animation of the traumatic event may include animating at least one of (1) a blunt force trauma applied to at least one body part, (2) a shearing force trauma applied to the at least one body part, or (3) a compression force trauma applied to the at least one body part. In some embodiments, the blunt force trauma may include a secondary penetration injury to the at least one body part.

In some examples, generating the animation of the traumatic event may include animating at least one of (1) a hyperextension of at least one body part, (2) a hyperflexion of the at least one body part, (3) a rotational force applied to the at least one body part, (4) a lateral force applied to the at least one body part, or (5) a distraction force caused by an excessive stretching of the at least one body part. In some embodiments, generating the animation of the traumatic event may include animating at least one of (1) a twisting injury, (2) a squatting injury, or (3) an injury caused by a change in position. In some embodiments, generating the animation of the traumatic event may include animating a non-contact injury.

BRIEF DESCRIPTION OF THE FIGURES

The accompanying drawings illustrate a number of example embodiments and are a part of the specification. Together with the following description, these drawings demonstrate and explain various principles of the instant disclosure.

DETAILED DESCRIPTION OF EXAMPLE EMBODIMENTS

Various embodiments of the disclosure are directed to systems and methods for simulating mechanisms of injury utilizing an objective impairment injury score risk model. As will be described in greater detail below, the systems and methods described herein may enable the utilization of simulation/animation tools to model mechanisms of injury for use by various parties of interest (e.g., medical providers, experts in personal injury litigation matters, etc.). A mechanism of injury refers to the way damage to a human body may occur as a result of an inciting event (e.g., trauma). Medical providers and experts are often queried as to the likelihood that a proposed mechanism of injury could have caused the trauma that leads to impairments and a related disability. Thus, the systems and methods described herein may be utilized to aid the aforementioned parties (among others) in understanding how disabilities result from causative trauma and to further aid in correlating impairment ratings incorporated into guidelines (e.g., American Medical Association (AMA) and/or similar guidelines).

In addition, the systems and methods described herein may improve the security of a computing device by protecting against the unauthorized sharing of the injury data through the use of blockchain technology. For example, the systems and methods herein may store the injury data as a plurality of linked blocks in a distributed computing system thereby preventing access to this sensitive data by malicious actors. In addition, the systems and methods described herein provide a machine-learning model capable of receiving, analyzing, and performing computations on large data sets on a computing device, functionality that may not be performed solely by a human being.

Embodiments of the disclosure now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

System Overview

Figure 1:
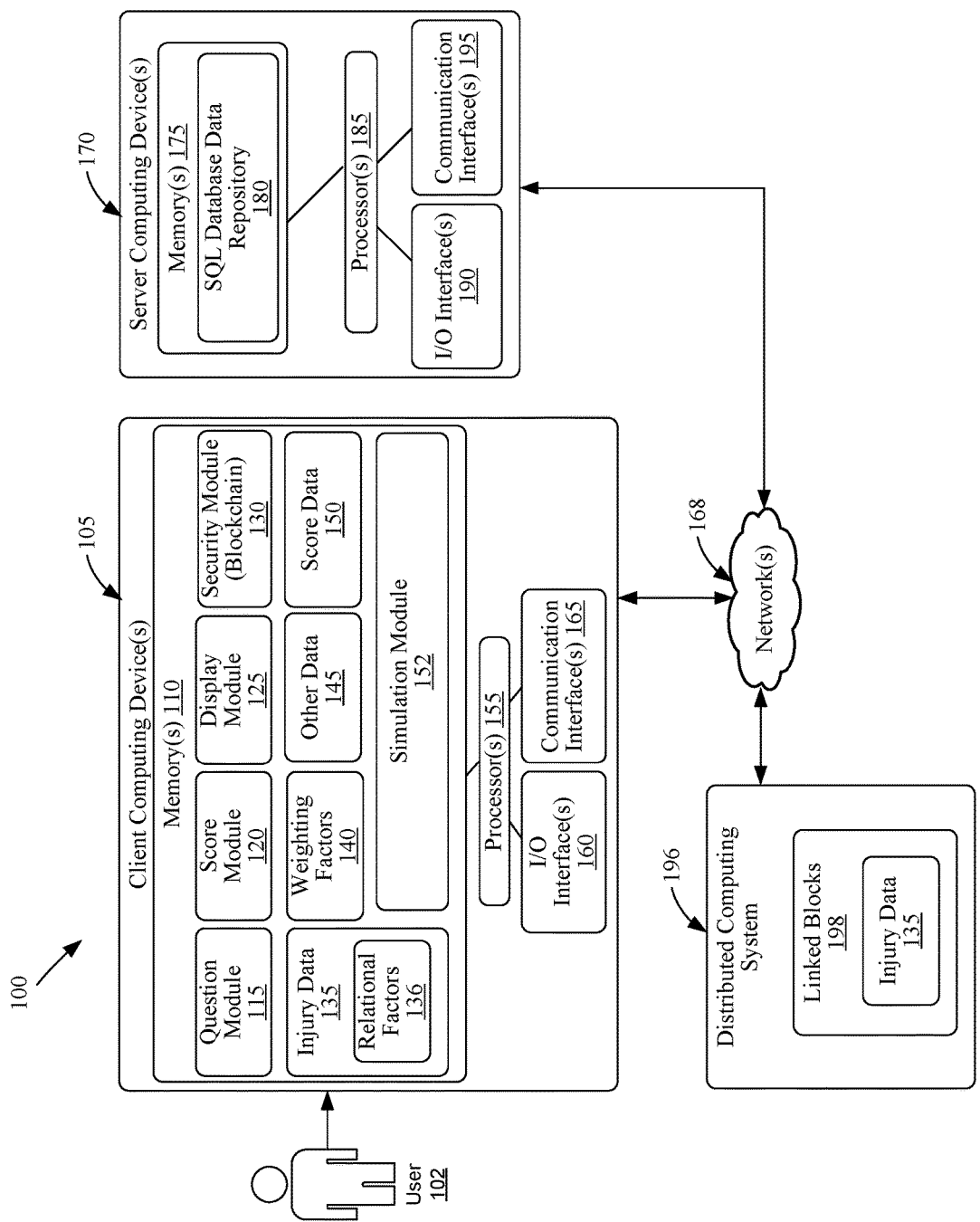
FIG. 1 illustrates a block diagram of an example system for simulating mechanisms of injury utilizing an objective impairment injury score risk model, according to an example embodiment.

FIG. 1 illustrates a block diagram of a system 100 for simulating mechanisms of injury utilizing an objective impairment injury score risk model. With reference to FIG. 1, system 100 may include a user 102, one or more client computing devices 105, one or more server computing devices 170, and a distributed computing system 196 (which may optionally include one or more client computing devices 105 and/or one or more server computing devices 170) in communication over network 168.

Client computing device 105 generally represents any type or form of computing device capable of reading computer-executable instructions. In some examples, client computing device 105 may include, but is not limited to, a mobile device (e.g., a mobile phone, Personal Digital Assistants (PDAs), smartphone, tablet computing device, etc.), a desktop computing device, a laptop computing device, servers, multimedia players, embedded systems, wearable devices (e.g., smart watches, smart glasses, etc.), gaming consoles, combinations of one or more of the same, or any other suitable computing device. Client computing device 105 may utilize one or more processors 155 to execute computer-readable instructions that facilitate the general operation of client computing device 105 and facilitating simulating mechanisms of injury utilizing an objective impairment injury score risk model.

In addition to having one or more processors 155, client computing device 105 may further include and/or be associated with one or more memory devices 110 (hereinafter "memory 110"), input/output ("I/O") interface(s) 160, and/or communication and/or network interface(s) 165. Memory 110 may be any non-transitory computer-readable medium, coupled to processor(s) 155, such as random access memory ("RAM"), read-only memory ("ROM"), and/or a removable storage device. Memory 110 may store a wide variety of data files and/or various program modules, such as a question module 115, score module 120, a display module 125, a security (e.g., blockchain) module 130, injury data 135, weighting factors 140, other data 145, score data 150, a simulation module 152, and an operating system ("OS") (not shown). The aforementioned data files and/or program modules may include any suitable data or instructions that facilitates the operation of client computing device 105 and/or interaction of client computing device 105 with one or more other components of the system 100. For example, question module 115 may be a component of a machine-learning model that includes instructions for generating one or questions for user 102 to determine weighting factors 140 associated with injury data 135. Additionally, score module 120 may be a component of a machine-learning model that determines an impairment injury score (e.g., score data 150) based on injury data 135 and weighting factors 140. Additionally, display module 125 may be a component of a machine-learning model configured to display an injury risk management report based on an impairment injury score (e.g., score data 150) to user 102. In some examples, the injury risk management report may also be included in score data 150. Additionally, security module 130 may be a component of a machine-learning model (or optionally a separate component on client computing device 105) configured perform a security action that protects against the unauthorized sharing of injury data 135 by storing injury data 135 as a group of linked blocks 198 in distributed computing system 196. In some examples, simulation module 162 may be configured to display a simulation (e.g., an animation of a sustained injury) describing a mechanism of the injury described in injury data 135, as will be described in greater detail below with respect to FIG. 5.

In some embodiments, injury data 135 may include one or more relational factors 136. The term "relational factors," as used herein, generally refers to any data that may be associated with the potential for a party to sustain an injury that the party subsequently incurs. In some examples, relational factors may include a number of subfactors including, without limitation, patient related factors, psychosocial factors, extrinsic factors, and/or economic factors. In one example, patient related factors may include the age and a previous injury history for an injured party prior to sustaining a current injury. For instance, in worker's compensation insurance claims, age is correlated to higher average payouts (i.e., the greater the age, the greater the average payout). In one example, psychosocial factors may include a current conditioning state and body habitus (e.g., physique or body build) state for an injured party prior to sustaining the current injury. In one example, extrinsic factors may include environmental and protective (e.g., the wearing of protective gear or equipment) conditions associated with an injured party prior to and/or during the sustaining of the current injury. In one example, economic factors may include employment relationships and employment type classification (e.g., sedentary, light, medium, heavy, very heavy, etc.) associated with an injured party prior to and/or during the sustaining of the current injury. For instance, hazardous classes of employment may include those involving lifting in the meat, fish, and/or poultry retail industries, hardware industries, and the automobile parts and accessories industry.

The term "mechanism of injury," as used herein, generally refers to the manner in which damage to a human body may occur as a result of an inciting event (e.g., trauma) and which may subsequently lead to physical impairment and related disability. A description of a mechanism of injury (or mechanism) may often be utilized in a number of medical fields associated with injury evaluation and/or treatment. For example, in the field of workers compensation, a mechanism of injury may be described as a "first report of injury" or a query as to how an injury happened.

The OS may be any suitable module that facilitates the general operation of the client computing device 105 as well as the execution of other program modules. For example, the OS may be, but is not limited to, a suitable mobile OS or a specially designed operating system. As desired, client computing device 105 may additionally include one or more communication modules that facilitate interaction with other computing devices and/or other communications functionality. For example, a suitable near field communication module, radio frequency module, Bluetooth module, or other suitable communication module may be included in client computing device 105.

With continued reference to client computing device 105, the one or more I/O interfaces 160 may facilitate communication between client computing device 105 and one or more input/output devices; for example, one or more user interface devices, such as a display, a keypad, a mouse, a pointing device, a control panel, a touch screen display, a remote control, a microphone, a speaker, etc., that facilitate user interaction with client computing device 105. The one or more network and/or communication interfaces 165 may facilitate connection of client computing device 105 to one or more suitable networks and/or communication links. In this regard, client computing device 105 may receive and/or communicate information to other components of the system 100, such as server computing device 170, and/or other devices and/or systems.

Server computing device 170 generally represents any type or form of computing device capable of reading computer-executable instructions. For example, as desired, server computing device 170 may include any number of processor-driven devices or systems, including but not limited to, cloud-based or dedicated application servers, a mobile computer, an application-specific circuit, a minicomputer, a microcontroller and/or any other processor-driven devices or systems configured to run certain software applications for receiving and processing large amounts of data. In some embodiments, server computing device 170 may utilize one or more processors 185 to execute computer-readable instructions that facilitate the general operation of server computing device 170 and that manage data in an SQL database data repository 180.

In addition to having one or more processors 185, server computing device 170 may further include and/or be associated with one or more memory devices 175 (hereinafter "memory 175"), input/output ("I/O") interface(s) 190, and/ or communication and/or network interface(s) 195. The memory 175 may be any non-transitory computer-readable medium, coupled to processor(s) 185, such as random access memory ("RAM"), read-only memory ("ROM"), and/or a removable storage device. Memory 175 may store a wide variety of data files and/or various program modules, such as SQL database data repository 180 and an operating system ("OS") (not shown). The aforementioned data files may include any suitable data that facilitates the operation of server computing device 170 and/or interaction of server computing device 170 with one or more other components of system 100. For example, data files may include SQL database data repository 180 that may be utilized for storing data accessed from various injury data sources utilized by a machine-learning model to determine an impairment injury score associated with a degree of impairment resulting from an injury described in injury data 135.

The OS may be suitable module that facilitates the general operation of server computing device 170, as well as the execution of other program modules. For example, the OS may be, but is not limited to, Microsoft Windows®, Apple OSX™, UNIX, LINUX, a mainframe computer operating system (e.g., IBM z/OS, MVS, OS/390, etc.), or a specially designed operating system.

Distributed computing system 196 may include any distributed configuration of client/and or server computing devices utilized for securely storing data (e.g., injury data 135) received from client computing device 105 and/or server computing device 170. In some examples, distributed computing system 196 may include a centralized distributed computing network including client computing device 105 (serving as a central node), server computing device 170, and one or more other computing devices (not shown) utilized for implementing blockchain security methods for data storage and/or retrieval. In other examples, distributed computing system 196 may include a decentralized distributed computing network including client computing device 105, server computing device 170, and one or more other computing devices (not shown) utilized for implementing blockchain security methods for data storage and/or retrieval.

Network(s) 168 may include any telecommunication or computer network (e.g., an intranet, a wide area network, a local area network, a personal area network, the Internet, a cellular or mobile network, etc.) that may be utilized to facilitate communication between client computing device 105, server computing device 170, and distributed computing system 196.

I/O interface 190 may facilitate communication between server computing device 170 and one or more input/output devices; for example, one or more user interface devices, such as a display, a keypad, a touch screen display, a microphone, a speaker, etc., that facilitate user interaction with server computing device 170. Network and/or communication interfaces 195 may facilitate connection of server computing device 170 to one or more suitable networks, for example, network 168. In this regard, server computing device 170 may receive and/or communicate information to other components of system 100 (such as client computing device 105 and/or distributed computing system 196).

System 100 as shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. Accordingly, embodiments of the disclosure should not be construed as being limited to any particular operating environment, system architecture, or device configuration.

Figure 2:
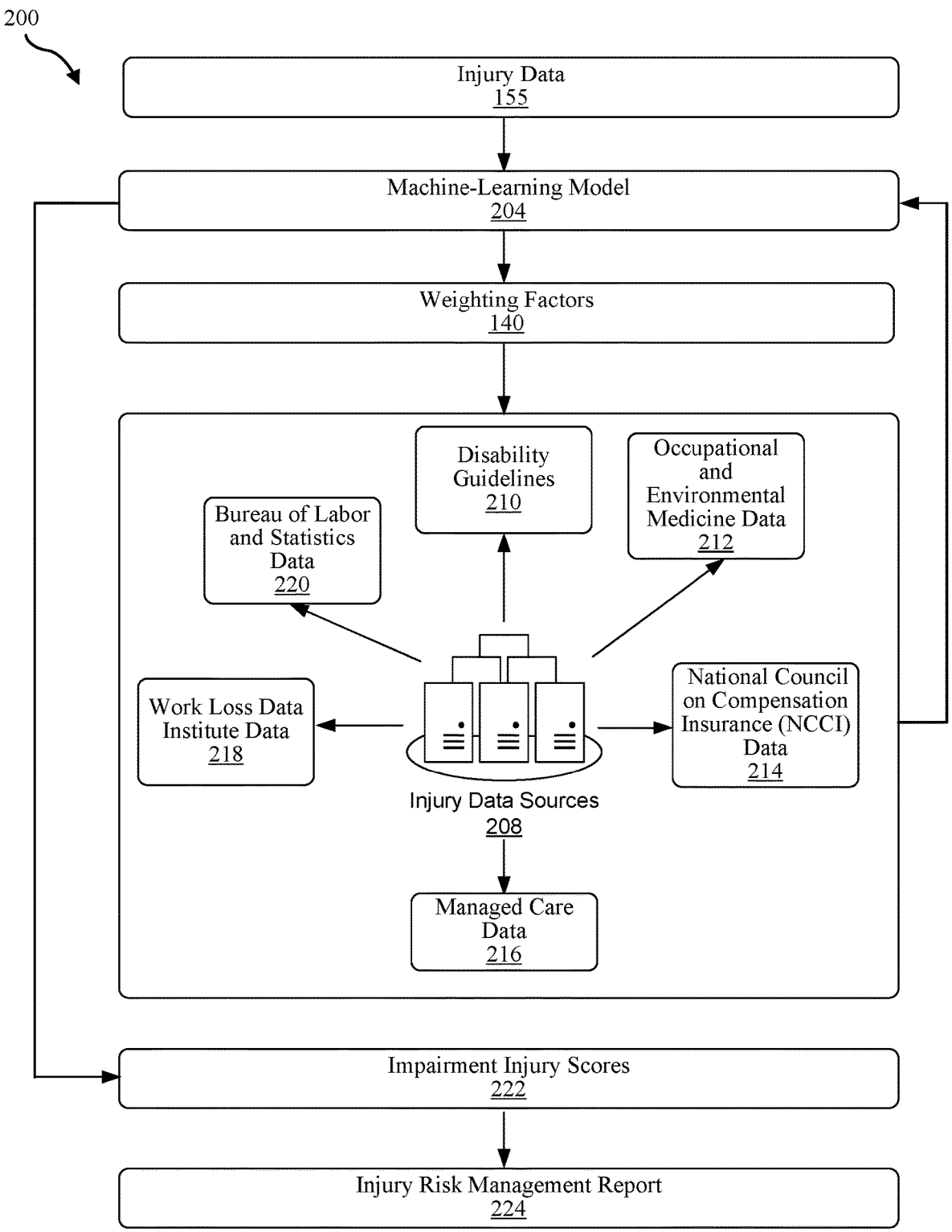
FIG. 2 illustrates a block diagram of an example system for utilizing an objecting impairment injury score risk model, according to an example embodiment.

FIG. 2 illustrates a block diagram of an example system 200 for utilizing an objecting impairment injury score risk model. The system 200 may include a machine-learning model 204. As will be described in greater detail below with respect to FIG. 3, machine-learning model 204 may receive injury data 135 describing one or more injuries from a user. Machine-learning model 204 may then apply weighting factors 140 (determined based the user's responses to generated questions based on injury data 135) to injury data 135. Next, machine-learning model 204 may access injury data sources 208 to retrieve data utilized in determining impairment injury scores 222. In some examples, injury data sources 208 may include, without limitation, disability guidelines 210 (e.g., the American Medical Association (AMA) guide to impairment and disability guidelines), occupational and environmental medicine data 212 (e.g., American College of Occupational and Environmental Medicine data), National Council on Compensation Insurance (NCCI) data 214, managed care data 216, Work Loss Data Institute data 218, and Bureau of Labor and Statistics data 220. Other injury data sources 208 may also be utilized. For example, in one embodiment, injury data sources 208 may further include existing military injury sources (e.g., Army, Air Force, Navy, Marine Corps, Coast Guard, etc.) associated with injuries incurred by military personnel while on duty.

In some embodiments, impairment injury scores 208 may include objectively determined values associated with a degree of impairment resulting from an injury described in injury data 135. Finally, based on impairment injury scores 222, an impairment injury score risk management report 224 may be generated and displayed (utilizing machine-learning model 204) to a user.

Operational Overview

Figure 3:
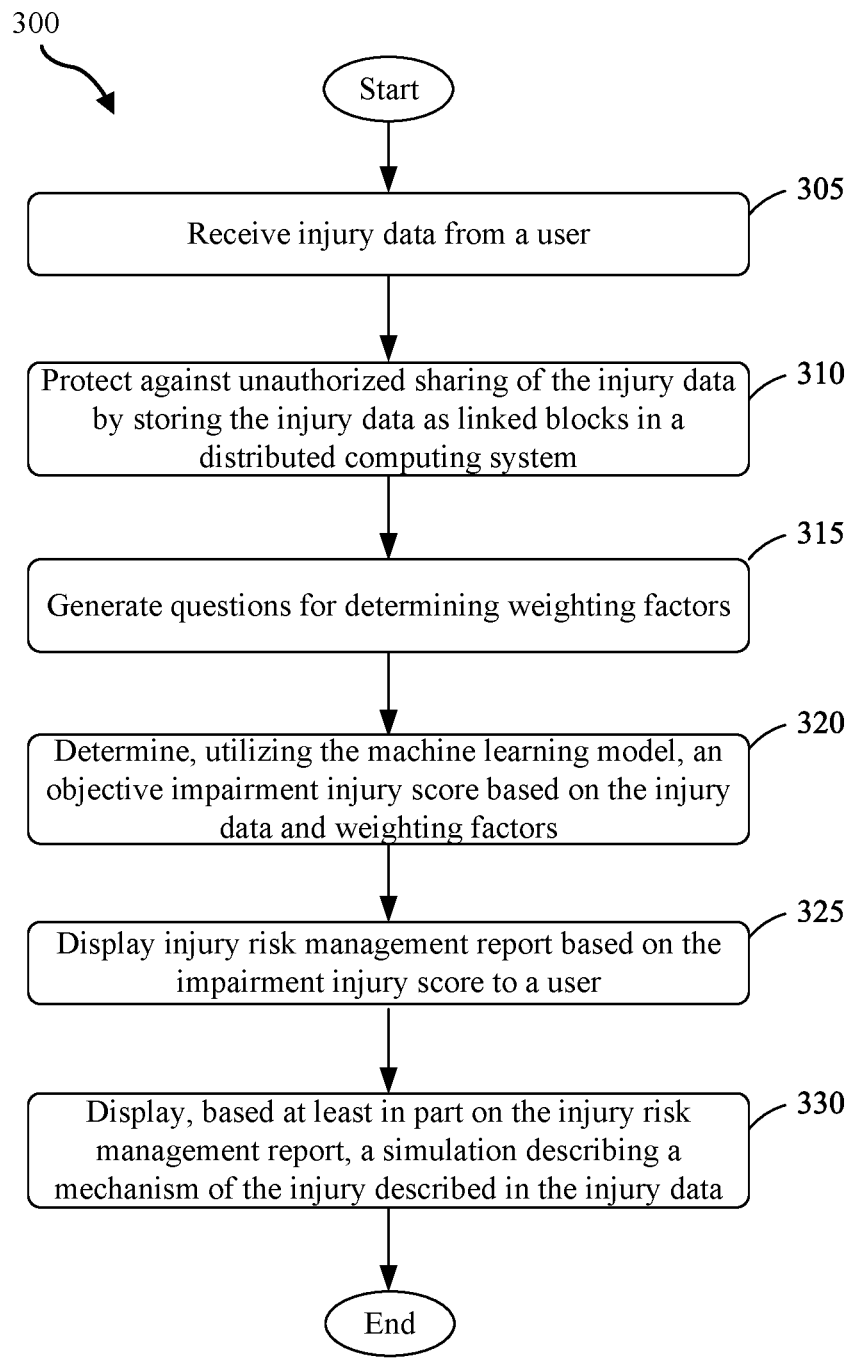
FIG. 3 illustrates a flow diagram of an example process for simulating mechanisms of injury utilizing an objective impairment injury score risk model, according to an example embodiment.

FIG. 3 illustrates a flow diagram of an example process 300 for simulating mechanisms of injury utilizing an objective impairment injury score risk, according to an example embodiment. The steps shown in FIG. 3 may be performed by any suitable computer-executable code and/or computing system, including system 100 in FIG. 1, system 200 in FIG. 2, and/or variations or combinations of one or more of the same. In one example, each of the steps shown in FIG. 3 may represent an algorithm whose structure includes and/or is represented by multiple sub-steps, examples of which will be provided in greater detail below.

As illustrated in FIG. 3, at step 305 one or more of the systems described herein may receive injury data from a user. For example, security module 130 may, as part of client computing device 105 in FIG. 1, receive injury data 135 from user 102 for encryption (e.g., via blockchain) and communicating to question module 115.

The term "injury data," as used herein, generally refers to any data describing injuries or disabilities associated with one or more injured parties. In some examples, injury data may include medical records maintained by a responsible party such as a medical provider, an insurance provider, and/or a legal services provider.

Security module 120 may receive injury data 135 in a variety of ways. In some examples, security module 120 may receive injury data 135 as one or more medical records associated with an injury from a medical provider. Additionally or alternatively, security module 120 may receive injury data 135 as one or more medical records associated with the injury from an insurance provider (e.g., for processing a claim). Additionally or alternatively, security module 120 may receive injury data 135 as one or more medical records associated with the injury from legal services provider (e.g., for review by an expert witness in a litigation matter).

At step 310, one or more of the systems described herein may protect against unauthorized sharing of the injury data by storing the injury data as linked blocks in a distributed computing system. For example, security module 120 may, as part of client computing device 105 in FIG. 1, protect against unauthorized sharing of injury data 135 by storing injury data 135 as linked blocks 198 in distributed computing system 196.

Security module 120 may store injury data 135 in a variety of ways. In some examples, security module 120 may store injury data 135 as a blockchain. In some examples, security module 130 the blockchain may include a smart contract between user 102 and a provider of injury data 135. In some embodiments, security module 120 may be configured to (1) receive a request for an impairment injury score rating (e.g., security module 120 may receive a request for an injury impairment injury score 222 from user 102) and (2) broadcast the request over a network (e.g., security module 120 may broadcast the request to distributed computing system 196 over network 168). Upon receiving the request, a network (e.g., distributed computing system 196) may validate the request using cryptography (i.e., blockchain encryption methods) to ensure privacy. A transaction (including the request, injury data 135 and weighting factors 140) may then be represented as one or more blockchain blocks to be stored and subsequently sent as data for independent medical examination (IME) and functional tests. Data generated by the IME and functional tests may then be sent to a data repository (e.g., SQL database data repository 180) for analysis by a machine-learning model utilizing explainable AI, analytics and prognostic report data which may be added as additional blocks to the existing blockchain. The request may then be completed with findings allowing an impairment injury score (e.g., an impairment injury score 222) to be used to value an injury based on an injured party's occupation (e.g., profession).

The term "blockchain," as used herein, generally refers to any decentralized and distributed or centralized and distributed network of computing devices in which information is secured through the construction of linked blocks representing the information. Each block may be utilized to store information up to a data capacity associated with the block, after which the block is added a link in the blockchain after receiving approval from every other device linked to the chain (e.g., protocol). In some examples, the protocol process includes requiring the generation of a cryptographic hash before a new block may be added to the chain. The security of the information stored in the blockchain is increased with each addition of a new block as the blockchain is copied onto every computing device associated with a single block. As a result, the computing power required to "break" the blockchain (i.e., gain unauthorized access to the stored information) increases exponentially with each new block. In some examples, a blockchain may be implemented according to a variety of models. These models may include, without limitation, Blockchain as a service (BaaS), development platforms, blockchain based software, network fee charge, blockchain professional services, and/or peer-to-peer (P2P) block chain business models. In some examples, a blockchain may be a permissive or private blockchain in which access to data (e.g., medical records) is restricted to only authorized individuals or entities having a provided unique address and password. In some examples, a private blockchain may be centralized and distributed blockchain providing customizability and control over the network to the individual or organization deploying as they may decide who participates in the network. As a result, fewer resources may be invested in competing to secure the network as compared to decentralized blockchains. Moreover, private blockchains may have a higher overall throughput as the hardware that the network runs on may be decided upon by the participants. In practice, this means that individuals or entities may use private blockchains to store sensitive information among trusted nodes without having to make the sensitive information public.

The term "smart contract," as used herein, generally refers to an automated contract between two parties on a blockchain with terms agreed upon by both parties. Once the terms of the contract are carried out, an algorithm may be utilized to deliver information and document the transaction on the blockchain. Smart contracts thus may eliminate the need for centralized authorities to verify the transactions including the delivery of information.

At step 315, one or more of the systems described herein may generate questions for determining weighting factors based on the injury data received at step 305. For example, machine-learning model 204 may, as part of client computing device 105 in FIG. 1, be utilized to generate one or more questions for user 102. Machine-learning model 204 may utilize the questions for receiving user answers to determine weighting factors 140 associated injury data 135. In one example, machine-learning model 204 may include question module 115 that may be configured to generate questions for determining weighting factors 140 based on injury data 135.

The term "machine-learning model," as used herein, generally refers to utilizing statistical techniques to provide computer systems the ability to "learn" (e.g., progressively improve performance on a specific task) from data, without being explicitly programmed. In some examples, machine learning models may utilize ensemble learning methods for classification, regression, and other tasks for generating one or more predictive outputs (e.g., outputs based on predictive modeling) based on provided input data. In some examples, machine-learning models may include artificial intelligence (AI), neural networks, cognitive modeling, and/or predictive modeling. In some embodiments, AI may include, without limitation, machine learning AI and explainable AI. Machine learning AI may include big data sets (e.g., data that is received in large amounts) that may be fed into an algorithm so that the algorithm train itself and learn. Explainable AI may include machine-learning techniques that make it possible for human users to understand, appropriately trust, and effectively manage AI. Explainable AI may include human led, machine supported methods including (i) a human that analyzes and produces insights using a portfolio of tools, (ii) the human makes decisions based on optimized machine prescriptions, and (iii) the human acts or executes the decisions. Additionally or alternatively, explainable AI may include machine led, human supported methods including (i) a machine analyzes and produces insights with human review, (ii) a human makes decisions based on optimized machine prescriptions, and (iii) the human acts or executes the decisions with machine oversight. Example machine learning models may include, without limitation, support vector machine models, logistic regression models, random forest models, and deep neural network (DNN) models.

Machine-learning model 204 may generate questions based on injury data 135 in a variety of ways. In some embodiments, machine-learning model 204 may generate queries for an occupation for an injured party associated with injury data 135, employment duties of an injured party associated with injury data 135, and/or income sources of an injured party associated with injury data 135. For example, if injury data 135 includes data relating to an anterior cruciate ligament (ACL) injury associated with an injured party, machine-learning model 204 may, based on rules defined by user 102, query user 102 whether the injured party has an occupation requiring a high level of physical activity (e.g., professional or amateur athletics, construction, public service, military service, etc.), the employment duties of the inured party (e.g., running back, soccer (football) player, dancer, construction worker, fireman, policeman, high risk military personnel (e.g., Navy Seals, Pararescue personnel, Army Rangers, Special Operations, Green Berets, etc.), and/or income sources such as contract values, endorsements (e.g., supplemental income), etc. Based on user-supplied answers to the aforementioned questions, machine-learning model 204 may determine weighting factors 140. Additionally or alternatively, user 102 may submit weighting factors 140 directly to machine-learning model 204 in response to query generated by machine-learning model 204.

Figure 4:
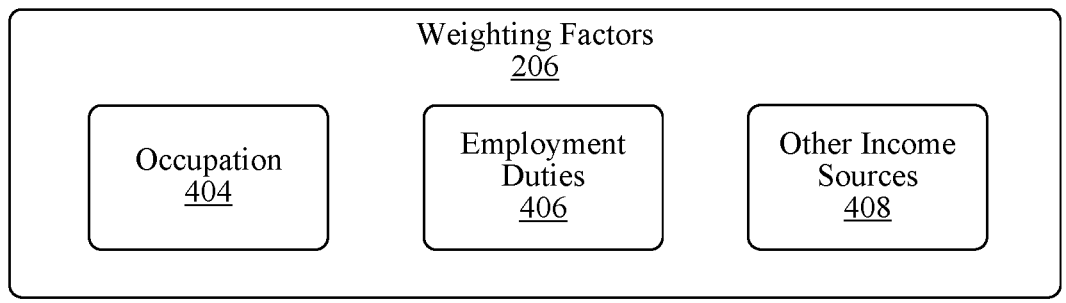
FIG. 4 illustrates a block diagram showing example weighting factors that may be utilized in the example systems for simulating mechanisms of injury utilizing an objective impairment injury score risk model, according to an example embodiment.

Turning now to FIG. 4 example weighting factors 140 are shown in accordance with various embodiments described herein. In some embodiments, weighting factors 140 may include occupation 404, employment duties 406, and/or other income sources 408. Returning now to step 315 of FIG. 3, machine-learning model 204 may utilize one or more weighting factors 140 in determining which injury data sources 208 to access in order to determine impairment injury scores 222.

At step 320, one or more of the systems described herein may determine, utilizing the machine-learning model, an impairment injury score based on the injury data and the weighting factors. For example, machine-learning model 204 may, as part of client computing device 105 in FIG. 1, be utilized to determine an impairment injury score 222 based on injury data 135 and weighting actors 140. In one example, machine-learning model 204 may include score module 120 that may be configured to determine an impairment injury score 222 based on injury data 135 and weighting factors 140. In some examples, an impairment injury score 222 may be a numerical value determined from one or more objective injury data sources (e.g., injury sources 208) that is associated with a degree of impairment resulting from an injury described in injury data 135. For example, an impairment injury score 222 for a professional athlete incurring a knee injury will have a higher numerical value (and thus representing a higher degree of impairment) as compared to an office worker with a desk job incurring the same injury due to the athlete's occupation and occupational duties requiring a higher level of knee function (e.g., for running, jumping, etc.) than the office worker's occupation and occupational duties. In addition, the athlete's potential income received for performing his/her primary occupation (as well as secondary income received from other sources (e.g., endorsement income)) may also be more adversely affected as compared to other occupations, thereby resulting in a higher impairment injury score 222. As another example, an impairment injury score 222 for a professional vocalist incurring a vocal cord injury will have a higher numerical value (and thus representing a higher degree of impairment) as compared to an instrumentalist incurring the same injury due to the vocalist's occupational duties requiring a higher level of larynx (i.e., voice box) function than the instrumentalist's occupational duties. In addition, the vocalist's potential income received for performing his/her primary occupational duties (as well as secondary income received from other sources (e.g., endorsement income) for performing the same duties) may also be more adversely affected, thereby resulting in a higher impairment injury score 222. As yet another example, an impairment injury score 222 for a surgeon incurring a musculoskeletal or nerve injury in their dominant hand will have a higher numerical value (and thus representing a higher degree of impairment) as compared to a medical practitioner who does not perform surgery (e.g., a family medicine or internal medicine physician) incurring the same injury due to the surgeon's occupational duties requiring a higher level of motor control and coordination. As yet another example, an impairment injury score 222 for a concert pianist or a concert violinist incurring a hand injury will also have a higher numerical value (and thus representing a higher degree of impairment) as compared to a vocalist in a musical group or band (who does not play an instrument) incurring the same injury due to their occupational duties requiring the use of one or both of their hands. As yet another example, an impairment injury score 222 for an active military person (e.g., an Air Force airman) involved in high risk duties (e.g. special operations duties involving a high degree of physical activity) incurring an orthopedic injury will have a higher numerical value (and thus representing a higher degree of impairment) as compared to light duty military personnel incurring the same injury.

Machine-learning model 204 may be utilized to determine impairment injury scores 222 in a in a variety of ways. In some embodiments, machine-learning model 204 may be utilized to (i) access, in real-time, injury data sources 208 to retrieve objective data associated with injury data 135 and weighting factors 140 and (ii) compute an impairment injury score 222 based on the objective data. For example, machine-learning model 204 may be utilized to retrieve objective data including one or more of disability guidelines 210 (e.g., American Medical Association (AMA) disability guidelines), occupational and environmental medicine data 212 (e.g., American College of Occupational and Environmental Medicine data), National Council on Compensation Insurance (NCCI) data 214, managed care data 216, Work Loss Data Institute data 218, and/or Bureau of Labor and Statistics data 220, from injury data sources 208. In some embodiments, the aforementioned objective data may be stored in SQL database data repository 180 on server computing device 170. In some examples, machine-learning model 204 may be configured to detect when each of injury data sources 208 has been updated and subsequently request the most recent data such that any current and/or new data (e.g., data updates) are received in real-time. Upon receiving the objective data from injury data sources 208, machine-learning model 204 may then apply weighting factors 140 to determine an impairment injury score 222. For example, occupation, employment duties, and income source weighting factors may be applied to information retrieved from disability guidelines 210, occupational and environmental medicine data 212, and work loss data institute data 218 regarding the effects of knee injuries on professional athletes or military personnel involved in high risk duty assignments with respect to the ability to return and/or the average length of their respective careers post-injury as well as loss of income due to being injured. In some examples, user 102 may review and evaluate the data retrieved from injury data sources 208 by machine-learning model 204 for accuracy and provide feedback thereon. For example, user 102 may be a physician who, based on his/her knowledge and experience, may determine if one or more of injury data sources 208 selected by machine-learning model 204 (or alternatively, any of the data retrieved from injury data sources 208) is applicable to injury data 135 and provide helpful feedback (e.g., discarding/failing inaccurate data or approving accurate data). Thus, in this way, user 102 may effectively "train" machine-learning model 204 to more accurately generate impairment injury scores 222. For example, based on the feedback received, machine-learning model 204 may be updated to generate different questions intended to elicit responses that will improve the selection of injury data sources 208 associated with injury data 135 and weighting factors 140.

At step 325, one or more of the systems described herein may display an injury risk management report based on the impairment injury score determined at step 320 to a user. For example, machine-learning model 204 may, as part of client computing device 105 in FIG. 1, be utilized to generate and display injury risk management report 224 to user 102.

Machine-learning model 204 may be utilized to generate and display injury risk management report 224 to user 102 in a in a variety of ways. In some embodiments, machine-learning model 204 generate a report including an impairment injury score 222 for an injured party associated with injury data 135 and weighting factors 140 for display on client computing device 105. In one example, injury risk management report 224 may describe a degree of impairment associated with an injury for an insurance claim. Additionally or alternatively, injury risk management report 224 may describe a degree of impairment associated with an injury for a litigation claim associated with an injury. For example, injury risk management report 224 may be utilized in support of satisfying evidentiary rules regarding the admissibility of expert witness testimony related to the effect an injury may have on an injured party's ability to continue to perform the duties of their chosen occupation, future income, etc.

At step 330, one or more of the systems described herein may display, based at least in part on the injury risk management report, a simulation describing a mechanism of the injury described in the injury data. For example, simulation module 152 may, as part of client computing device 105 in FIG. 1, be utilized to generate a simulation (e.g., an animation) of the injury described in injury data 135 (which may be shown in injury risk management report 224) to user 102. The functionality of simulation module 152 in generating the simulation of the injury will be described in greater detail below with respect to FIGS. 5-9.

The example process 300 may end following step 330.

Figure 5:
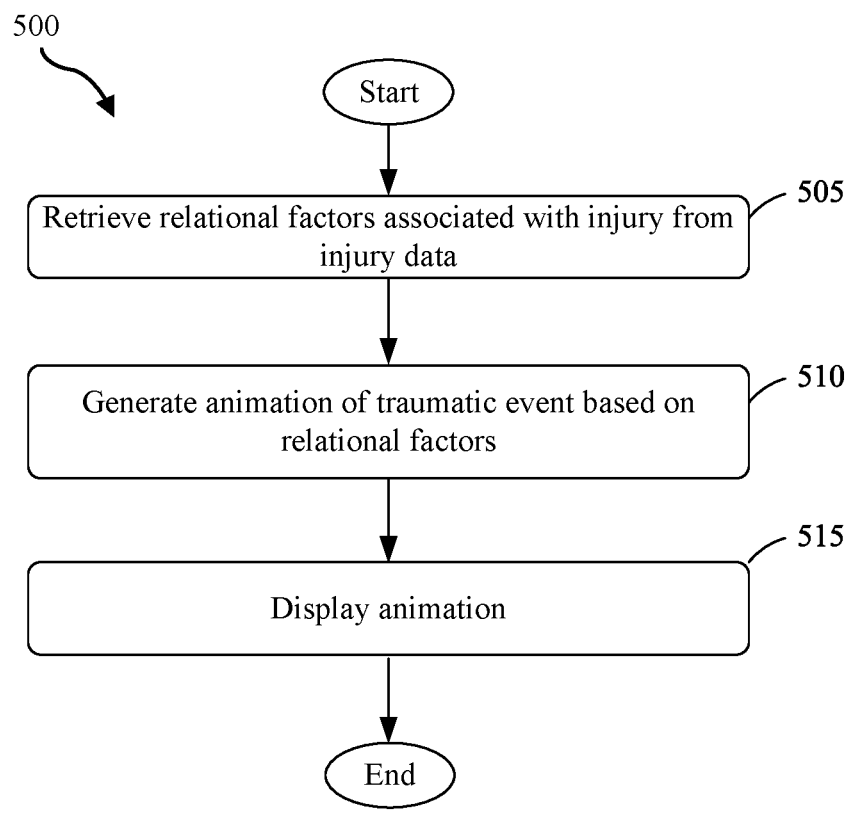
FIG. 5 illustrates a flow diagram of an example process for displaying a simulation describing a mechanism of injury, according to an example embodiment.

FIG. 5 illustrates a flow diagram of an example process 500 for displaying a simulation describing a mechanism of injury. The steps shown in FIG. 5 may be performed by any suitable computer-executable code and/or computing system, including system 100 in FIG. 1, system 200 in FIG. 2, process 300 of FIG. 3, and/or variations or combinations of one or more of the same. In one example, each of the steps shown in FIG. 5 may represent an algorithm whose structure includes and/or is represented by multiple sub-steps, examples of which will be provided in greater detail below.

As illustrated in FIG. 5, at step 505 one or more of the systems described herein may retrieve relational factors associated with an injury from injury data. For example, simulation module 152 may, as part of client computing device 105 in FIG. 1, retrieve relational factors 136 from injury data 135. In some examples, injury data 135 (as well as relational factors 136) may be retrieved from injury risk management report 224 generated by machine-learning model 204 for display to user 102.

Simulation module 152 may retrieve relational factors 136 in a variety of ways. In some examples, simulation module 152 may retrieve relational factors 136 as a group of subfactors that may include, without limitation, patent related factors associated with an injured party, psychosocial factors associated with an injured part, extrinsic factors associated with an injured party, and/or economy factors associated with an injured party. In one example, patient related factors may include the age and a previous injury history for an injured party prior to sustaining a current injury. In one example, psychosocial factors may include a current conditioning and body habitus (e.g., physique or body build) state for an injured party prior to sustaining the current injury. In one example, extrinsic factors may include environmental and protective (e.g., the wearing of protective gear or equipment) conditions associated with an injured party prior to and/or during the sustaining of the current injury. In one example, economic factors may include employment relationships and employment type classification (e.g., sedentary, light, medium, heavy, very heavy, etc.) associated with an injured party prior to and/or during the sustaining of the current injury.

At step 510, one or more of the systems described herein may generate an animation of a traumatic event based on the relational factors retrieved at step 510. For example, simulation module 152 may, as part of client computing device 105 in FIG. 1, generate an animation of a traumatic event based on relational factors 136. In some examples, the animation generated by simulation module 152 may include the generation of one or more avatars representing a human body as it incurs an injury described in injury risk management report 224. Additionally or alternatively, the animation generated by simulation module 152 may include the generation of one or more human body parts as it incurs an injury described in injury risk management report 224. In some examples, simulation module 152 may be configured to construct and utilize a computer-based model for simulating injuries described in injury risk management report 224.

Simulation module 152 may generate an animation of a traumatic event in a variety of ways. In some examples, simulation module 152 generate an animation of a blunt force trauma applied to at least one body part. In one example, the animation of the blunt force trauma may further include animating a secondary penetration injury to the at least one body part. Additionally or alternatively, simulation module 152 may generate an animation of a shearing force trauma applied to the at least one body part. Additionally or alternatively, simulation module 152 may generate an animation of a compression force trauma applied to the at least one body part. Additionally or alternatively, simulation module 152 may generate an animation of a hyperextension of at least one body part. Additionally or alternatively, simulation module 152 may generate an animation of a hyperflexion of at least one body part. Additionally or alternatively, simulation module 152 may generate an animation of a rotational force applied to at least one body part. Additionally or alternatively, simulation module 152 may generate an animation of a lateral force applied to at least one body part. Additionally or alternatively, simulation module 152 may generate an animation of a distraction force caused by an excessive stretching of at least one body part. Additionally or alternatively, simulation module 152 may generate an animation of a twisting injury sustained by at least one body part. Additionally or alternatively, simulation module 152 may generate an animation of a squatting injury sustained by at least one body part. Additionally or alternatively, simulation module 152 may generate an animation of an injury cause by a change in position of at least one body part. Additionally or alternatively, simulation module 152 may generate an animation of a non-contact injury sustained by at least one body part.

At step 515, one or more of the systems described herein may display the animation generated at step 510. For example, simulation module 152 may, as part of client computing device 105 in FIG. 1, display the animation of a traumatic event based on relational factors 136 to user 102.

The example process 500 may end following step 515.

Figure 6:
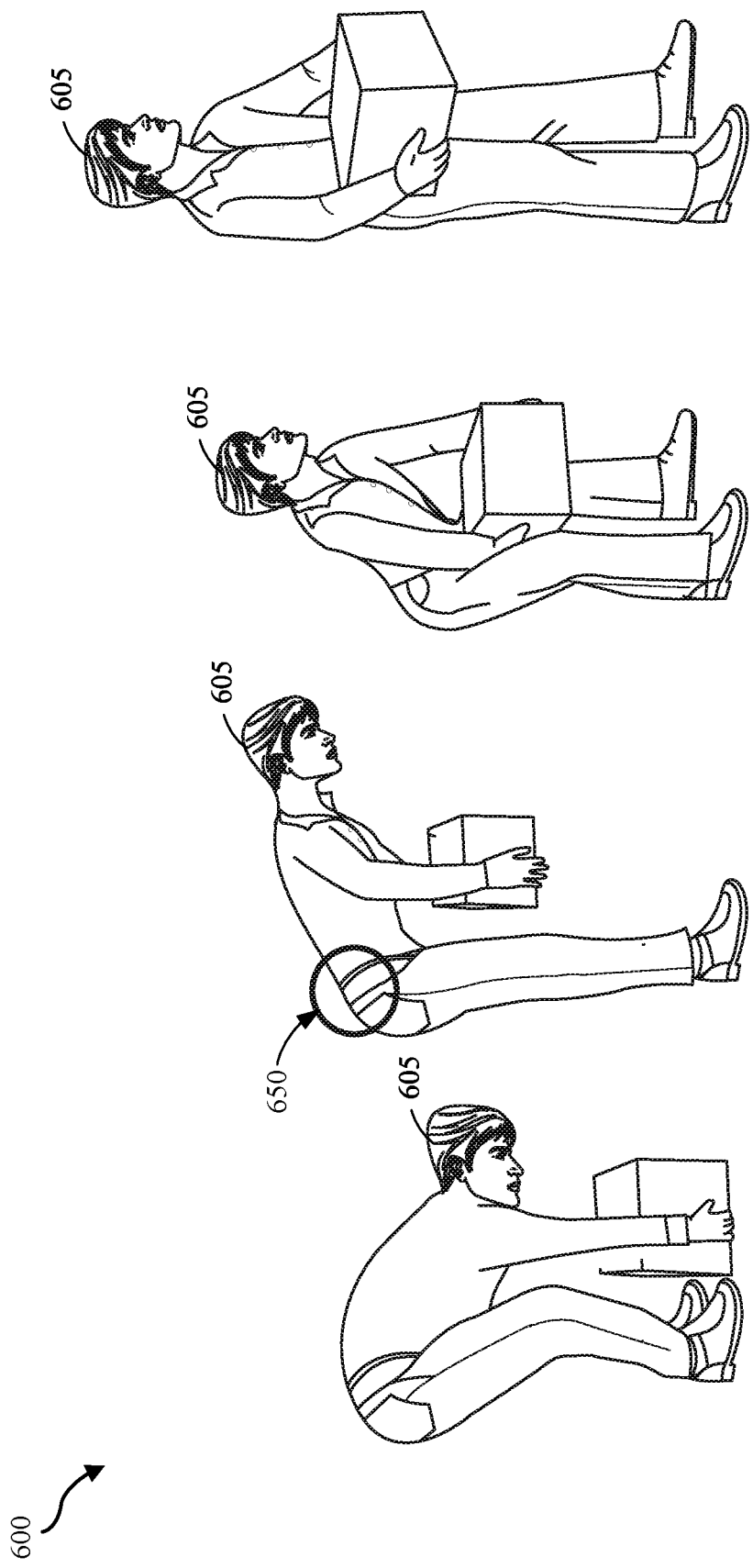
FIG. 6 illustrates an example injury simulation displayed by the example systems for simulating mechanisms of injury utilizing an objective impairment injury score risk model, according to an example embodiment.

Turning now to FIGS. 6-9, example animations that may be generated by simulation module 152 are shown. For example, FIG. 6 shows a series of frames 600 (i.e., an animation) of a human avatar 605 sustaining a back injury 650 due to improperly lifting a box. In some examples, human avatar 605 may represent an actual injured party sustaining an injury described in injury management report 224 and account for various relational factors 136. For example, based on injury management report 224 and relational factors 136, the injured party may have sustained back injury 650 by ignoring proper lifting techniques while attempting to lift a 50-pound box with his back (instead of lifting with his legs). Additionally or alternatively, the injured party may have had a preexisting injury from an automobile accident prior to sustaining back injury 650. Additionally or alternatively, the injured party may have attended employee training for safe lifting techniques before (e.g., 2 months) sustaining back injury 650.

Figure 7:
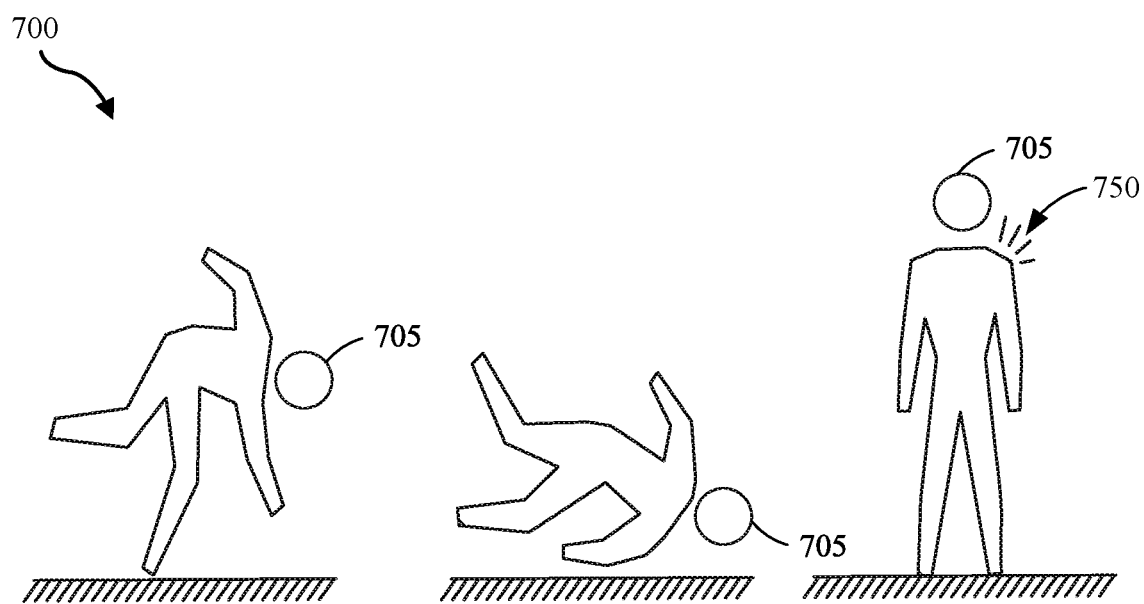
FIG. 7 illustrates another example injury simulation displayed by the example systems for simulating mechanisms of injury utilizing an objective impairment injury score risk model, according to an example embodiment.

Turning now to FIG. 7, a series of frames 700 (i.e., an animation) of a human avatar 705 sustaining a shoulder injury 750 resulting from a fall, are shown. In some examples, human avatar 705 may represent an actual injured party sustaining an injury described in injury management report 224 and account for various relational factors 136. For example, based on injury management report 224 and relational factors 136, the injured party may have sustained shoulder injury 750 by falling when his arm was extended causing the injured party's shoulder to come into contact with the ground thereby resulting in a direct blow to the shoulder.

Figure 8:
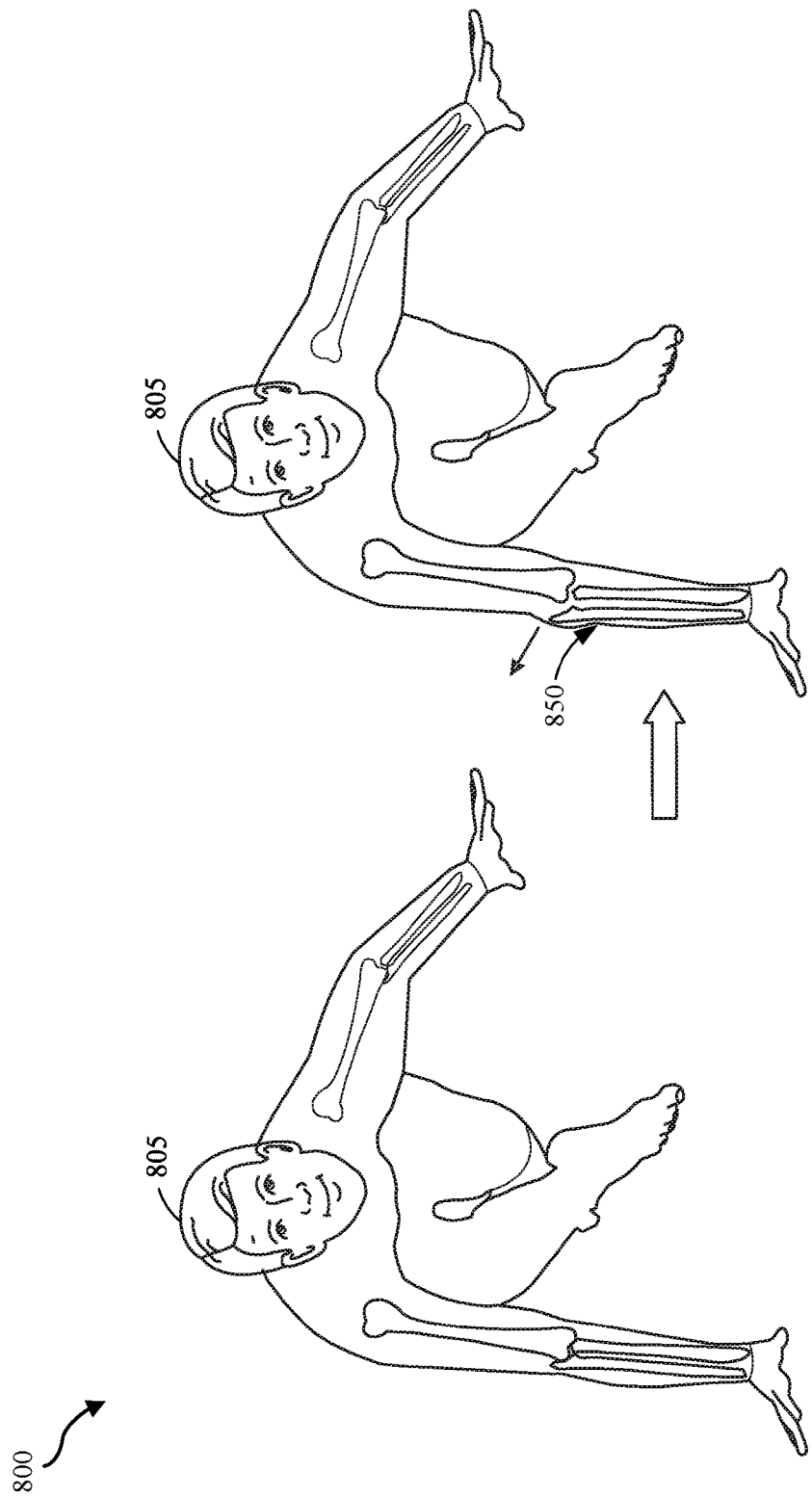
FIG. 8 illustrates another example injury simulation displayed by the example systems for simulating mechanisms of injury utilizing an objective impairment injury score risk model, according to an example embodiment.

Turning now to FIG. 8, a series of frames 800 (i.e., an animation) of a human avatar 805 sustaining a forearm injury 850 (e.g., a fracture) resulting from a fall, are shown. In some examples, human avatar 805 may represent an actual injured party sustaining an injury described in injury management report 224 and account for various relational factors 136. For example, based on injury management report 224 and relational factors 136, the injured party may have sustained forearm injury 850 by falling on his hand when his arm was extended such that the impact from the ground resulted in forces transmitted through his forearm thereby causing a fracture of the radius and ulna bones which make up the forearm.

Figure 9:
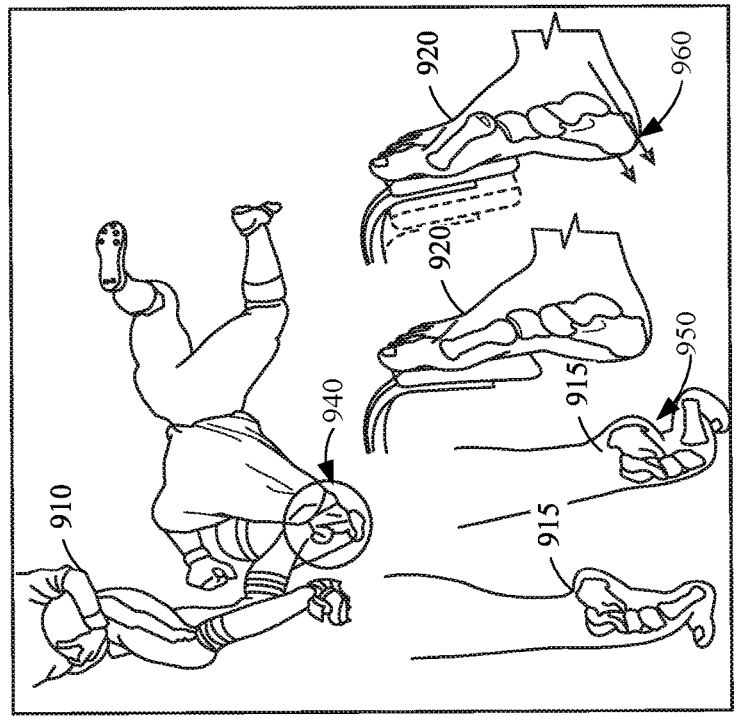
FIG. 9 illustrates another example injury simulation displayed by the example systems for simulating mechanisms of injury utilizing an objective impairment injury score risk model, according to an example embodiment.
Figure 9:
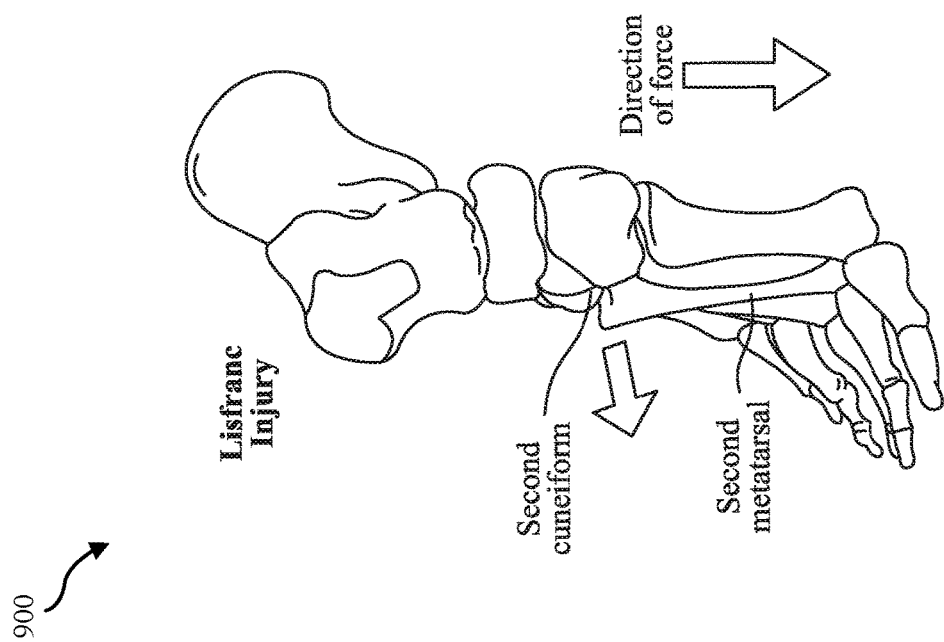

Turning now to FIG. 9, a group of animations 900 showing a foot injury (e.g., a Lisfranc injury). In one example, an animation 900 may include a series of frames (of which one is shown) illustrating a human avatar 905 (e.g., a football player) incurring a Lisfranc injury 940 as a result of a tackle to the back of the leg. In another example, an animation 900 may include a series of fames showing a foot 915 of a dancer incurring a Lisfranc injury 950 while performing a ballet movement. In yet another example, an animation 900 may include a series of frames showing a driver's foot 920 incurring a Lisfranc injury 960 while operating a motor vehicle.

Various embodiments of the invention are described above with reference to block and flow diagrams of systems, methods, apparatuses, and/or computer program products according to example embodiments. It will be understood that one or more blocks of the block diagrams and flow diagrams, and combinations of blocks in the block diagrams and the flow diagrams, respectively, can be implemented by computer-executable program instructions. Likewise, some blocks of the block diagrams and flow diagrams may not necessarily need to be performed in the order presented, or may not necessarily need to be performed at all, according to some embodiments.

Various block and/or flow diagrams of systems, methods, apparatus, and/or computer program products according to example embodiments are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments.

The computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flow diagram block or blocks. The computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks.

As an example, embodiments may provide for a computer program product, comprising a computer-readable medium having a computer-readable program code or program instructions embodied therein, said computer-readable program code adapted to be executed to implement one or more functions specified in the flow diagram block or blocks. The term "computer-readable medium," as used herein, generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special purpose, hardware-based computer systems that perform the specified functions, elements or steps, or combinations of special purpose hardware and computer instructions.

The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the exemplary embodiments disclosed herein.

In addition, one or more of the modules described herein may transform data, physical devices, and/or representations of physical devices from one form to another. Additionally or alternatively, one or more of the modules recited herein may transform a processor, volatile memory, non-volatile memory, and/or any other portion of a physical computing device from one form to another by executing on the computing device, storing data on the computing device, and/or otherwise interacting with the computing device.

Many modifications and other embodiments of the invention set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A computer-implemented method for simulating mechanisms of injury utilizing an objective impairment injury score risk model, at least a portion of the method being performed a computing device comprising at least one processor, the method comprising:

receiving, by the computing device, injury data from a user;

performing, by the computing device, a security action that protects against unauthorized sharing of the injury data by storing the injury data as a plurality of linked blocks in a distributed computing system;

generating, by the computing device and utilizing a machine-learning model, one or more questions for the user, wherein the questions are utilized for receiving user answers to determine a plurality of weighting factors associated with the injury data;

determining, by the computing device and utilizing the machine-learning model, an impairment injury score based on the injury data and the weighting factors, wherein the impairment injury score comprises an objectively determined value associated with a degree of impairment resulting from an injury described in the injury data;

displaying, by the computing device, an injury risk management report based on the impairment injury score to the user; and displaying, by the computing device and based at least in part on the injury risk management report, a simulation describing a mechanism of the injury described in the injury data.

2. The computer-implemented method of claim 1, wherein displaying the simulation describing the mechanism of the injury comprises:

retrieving one or more relational factors associated with the injury from the injury data; and displaying the simulation based on the relational factors.

3. The computer-implemented method of claim 2, wherein the relational factors comprise at least one of:

patient related factors associated with an injured party;
psychosocial factors associated with the injured party;
extrinsic factors associated with the injured party; or
economy factors associated with the injured party.

4. The computer-implemented method of claim 2, wherein the relational factors are utilized to determine a potential for incurring the injury described in the injury data.

5. The computer-implemented method of claim 1, wherein displaying the simulation describing the mechanism of the injury comprises generating an animation of a traumatic event causing at least one of:

a spinal injury;
a musculoskeletal injury; or
an internal organ injury.

6. The computer-implemented method of claim 5, wherein generating the animation of the traumatic event comprises animating at least one of:

a blunt force trauma applied to at least one body part;
a shearing force trauma applied to the at least one body part; or
a compression force trauma applied to the at least one body part.

7. The computer-implemented method of claim 6, wherein the blunt force trauma further comprises a secondary penetration injury to the at least one body part.

8. The computer-implemented method of claim 5, wherein generating the animation of the traumatic event comprises animating at least one of:

a hyperextension of at least one body part;
a hyperflexion of the at least one body part;
a rotational force applied to the at least one body part;
a lateral force applied to the at least one body part; or
a distraction force caused by an excessive stretching of the at least one body part.

9. The computer-implemented method of claim 5, wherein generating the animation of the traumatic event comprises animating at least one of:

a twisting injury;
a squatting injury; or
an injury caused by a change in position.

10. The computer-implemented method of claim 5, wherein generating the animation of the traumatic event comprises animating a non-contact injury.

11. A system for simulating mechanisms of injury utilizing an objective impairment injury score risk model, the system comprising:

at least one processor; and
at least one memory storing computer-executable instructions that when executed by the at least one processor, cause the system to:

receive, by a computing device, injury data from a user;

perform, by the computing device, a security action that protects against unauthorized sharing of the injury data by storing the injury data as a plurality of linked blocks in a distributed computing system;

generate, by the computing device and utilizing a machine-learning model, one or more questions for the user, wherein the questions are utilized for receiving user answers to determine a plurality of weighting factors associated with the injury data;

determine, by the computing device and utilizing the machine-learning model, an impairment injury score based on the injury data and the weighting factors, wherein the impairment injury score comprises an objectively determined value associated with a degree of impairment resulting from an injury described in the injury data;

display, by the computing device, an injury risk management report based on the impairment injury score to the user; and display, by the computing device and based at least in part on the injury risk management report, a simulation describing a mechanism of the injury described in the injury data.

12. The system of claim 11, wherein the simulation describing the mechanism of the injury is displayed by:

retrieving one or more relational factors associated with the injury from the injury data; and displaying the simulation based on the relational factors.

13. The system of claim 12, wherein the relational factors comprise at least one of:

patient related factors associated with an injured party;
psychosocial factors associated with the injured party;
extrinsic factors associated with the injured party; or
economy factors associated with the injured party.

14. The system of claim 12, wherein the relational factors are utilized to determine a potential for incurring the injury described in the injury data.

15. The system of claim 11, the simulation describing the mechanism of the injury is displayed by generating an animation of a traumatic event causing at least one of:

a spinal injury;
a musculoskeletal injury; or
an internal organ injury.

16. The system of claim 15, the animation of the traumatic event is generated by animating at least one of:

a blunt force trauma applied to at least one body part;

a shearing force trauma applied to the at least one body part; or a compression force trauma applied to the at least one body part.

17. The system of claim 16, wherein the blunt force trauma further comprises a secondary penetration injury to the at least one body part.

18. The system of claim 15, wherein the animation of the traumatic event is generated by animating at least one of:

a hyperextension of at least one body part;

a hyperflexion of the at least one body part;

a rotational force applied to the at least one body part;

a lateral force applied to the at least one body part; or a distraction force caused by an excessive stretching of the at least one body part.

19. The system of claim 15, wherein the animation of the traumatic event is generated by animating at least one of:

a twisting injury;

a squatting injury; or an injury caused by a change in position.

20. A non-transitory computer-readable medium comprising one or more computer-executable instructions that, when executed by at least one processor of a computing device, cause the computing device to:

receive injury data from a user;

perform a security action that protects against unauthorized sharing of the injury data by storing the injury data as a plurality of linked blocks in a distributed computing system;

generate, utilizing a machine-learning model, one or more questions for the user, wherein the questions are utilized for receiving user answers to determine a plurality of weighting factors associated with the injury data;

determine, utilizing the machine-learning model, an impairment injury score based on the injury data and the weighting factors, wherein the impairment injury score comprises an objectively determined value associated with a degree of impairment resulting from an injury described in the injury data;

display an injury risk management report based on the impairment injury score to the user; and display, based at least in part on the injury risk management report, a simulation describing a mechanism of the injury described in the injury data.

* * * * *